United States Patent [19]

Döring et al.

[11] 4,266,059

[45] May 5, 1981

[54] PROCESS FOR THE PREPARATION OF 2,4,5-TRICHLOROPYRIMIDINE

[75] Inventors: Fritz Döring, Odenthal; Gunther Beck, Leverkusen; Gerhard Dankert, Cologne, all of Fed. Rep. of Germany

[73] Assignee: Bayer Aktiengesellschaft, Leverkusen, Fed. Rep. of Germany

[21] Appl. No.: 99,126

[22] Filed: Nov. 30, 1979

[30] Foreign Application Priority Data

Dec. 22, 1978 [DE] Fed. Rep. of Germany ....... 2855660

[51] Int. Cl.$^3$ ............................................ C07D 239/30
[52] U.S. Cl. .................................................. 544/334
[58] Field of Search .......................................... 544/334

[56] References Cited

U.S. PATENT DOCUMENTS

| | | | |
|---|---|---|---|
| 3,682,916 | 8/1972 | Findeisen et al. ................... | 544/334 |
| 4,026,892 | 5/1977 | Beck et al. ........................... | 544/334 |
| 4,140,857 | 2/1979 | Beck et al. ........................... | 544/334 |
| 4,211,869 | 7/1980 | Beck et al. ........................... | 544/334 |

FOREIGN PATENT DOCUMENTS 578933  5/1959  Belgium .
2307863  8/1974  Fed. Rep. of Germany .

OTHER PUBLICATIONS

R. Braden et al., Angewandte Chemie, 82 (1970), p. 78 & 79.

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

2,4,5-Trichloropyrimidine is obtained by reacting 2-cyanoethyl isocyanide dichloride with hydrogen chloride and then reacting the product with chlorine.

9 Claims, No Drawings

PROCESS FOR THE PREPARATION OF 2,4,5-TRICHLOROPYRIMIDINE

The present invention relates to a new process for the preparation of 2,4,5-trichloropyrimidine.

The process is characterised in that 2-cyanoethyl isocyanide dichloride of the formula $$NC-CH_2-CH_2-N=CCl_2 \quad (I)$$

is first reacted with hydrogen chloride and the product is then reacted with chlorine, preferably in an inert solvent.

In general, the reaction with hydrogen chloride takes place in a temperature range from −20° to 50° C., preferably between 0° and 30° C. A colourless precipitate thereby forms. Hydrogen chloride is generally passed in until no further precipitate forms. 2 mols of hydrogen chloride are generally required per mol of (I) to bring the formation of the precipitate to completion. Larger amounts of hydrogen chloride do not have an adverse effect on the reaction.

The reaction can also be carried out under an increased pressure of HCl. The rate of the reaction with hydrogen chloride depends, of course, on the pressure, that is to say the reaction is more rapid under a higher pressure of HCl.

Under a normal pressure of HCl, the reaction in general goes substantially to completion in the course of about 5–30 hours, preferably 10–20 hours, and under increased pressure the time is correspondingly shorter.

The reaction with hydrogen chloride is, however, also dependent upon the nature of the inert solvent used. Inert solvents which may be mentioned are: 2,4,5-trichloropyrimidine itself, phosphorus oxychloride, thionyl chloride and chloroform.

2,4,5-Trichloropyrimidine and phosphorus oxychloride are particularly preferred. In these solvents, the reaction goes virtually to completion under a normal pressure of HCl in the region of 10–20 hours, whilst in chloroform and in thionyl chloride, the reaction with hydrogen chloride is not yet complete in comparable periods of time. However, in these cases unreacted 2-cyanoethyl isocyanide dichloride can be separated off from the 2,4,5-trichloropyrimidine formed by fractional distillation during working up of the chlorination batch by distillation, and can be passed to renewed reaction with HCl and chlorine.

The reaction with chlorine which follows after the reaction with hydrogen chloride is generally carried out at about 40°–150° C., preferably at about 50°–80° C. In this reaction, chlorine is passed in until no further absorption takes place, but at least long enough for the precipitate formed by the preceding reaction with hydrogen chloride to go completely into solution. Provided that the reaction with HCl was quantitative, about 2 mols of chlorine per mol of (I) are generally required for this reaction. It is, of course, possible to use an excess of chlorine.

The end of the reaction with chlorine is in general recognized by the fact that the suspension has changed into a homogeneous solution. This main chlorination reaction is preferably carried out between 50° and 80° C. In practice, chlorination is also continued for about a further 2–5 hours, using a stream of chlorine in slight excess (recognizable by the greenish colour of the off-gas), after a homogeneous solution has been achieved, for the purpose of increasing the yield of 2,4,5-trichloropyrimidine. The upper limit of the preferred temperature range for the main chlorination reaction, that is to say, for example, 80° C., is sufficient for this post-chlorination reaction; however, it is also possible to increase the temperature up to 150° C. during the post-chlorination reaction.

To avoid slight further chlorination of the 2,4,5-trichloropyrimidine formed or employed as the solvent to give tetrachloropyrimidine, it is appropriate to carry out the entire chlorination reaction with exclusion of light.

To carry out the process according to the invention the liquid starting compound of the formula (I) is mixed with 2–20, preferably 5–10, parts by weight of one of the inert solvents mentioned, and HCl gas (at least 2 mols per mol of I) is passed over a period of 5–30, preferably 10–20, hours. However, it is also possible to dissolve the entire amount of HCl used in the mixture of (I) and the solvent right at the start and then to stir the mixture further until the reaction has ended. The subsequent chlorination is then preferably carried out at 50°–80° C., optionally at up to 150° C., and appropriately with exclusion of light.

The reactions with HCl and/or with chlorine can, of course, also be carried out continuously.

The mixture is worked up in a customary manner by fractional distillation.

2,4,5-Trichloropyrimidine can be converted into tetrachloropyrimidine by gas phase chlorination (British Patent Specification No. 1,201,228). Tetrachloropyrimidine is suitable as a reactive component for the preparation of reactive dyestuffs (compare, for example, Belgian Patent Specification No. 578,933). Moreover, 2,4,5-trichloropyrimidine has fungicidal and sporicidal properties (compare U.S. Pat. No. 3,227,612) and can be used for the preparation of reactive dyestuffs with dichloropyrimidyl groups, dyestuffs with amino or amide groups being employed as starting compounds.

2-Cyanoethyl isocyanide dichloride (I) is prepared, for example, by reacting (2-cyanoethyl)-formamide (II) with thionyl chloride and chlorine according to the equation $$NC-CH_2-CH_2-NH-CHO + SOCl_2 + Cl_2 \longrightarrow \quad (II)$$
$$NC-CH_2-CH_2-N=CCl_2 + SO_2 + 2HCl \quad (I)$$

at temperatures of 40°–80° C., preferably 50°–75° C. Instead of thionyl chloride, corresponding amounts of phosgene can also advantageously be used in this reaction, according to the equation $$NC-CH_2-CH_2-NH-CHO + COCl_2 + Cl_2 \longrightarrow \quad (II)$$
$$NC-CH_2-CH_2-N=CCl_2 + CO_2 + 2HCl \quad (I)$$

(2-Cyanoethyl)-formamide (II) can be prepared in a known manner (French Patent Specification No. 976,959), for example from formamide and acrylonitrile.

The preparation of (I) by means of phosgene and chlorine is carried out in inert solvents, such as, for example, chloroform or 2,4,5-trichloropyrimidine. This enables the preparation of 2,4,5-trichloropyrimidine from (2-cyanoethyl)-formamide (II) to be carried out as a "one-pot" process without intermediate isolation of 2-cyanoethyl isocyanide dichloride (I).

The present invention accordingly furthermore relates to a process for the preparation of 2,4,5-trichloropyrimidine, which is characterised in that (2-cyanoethyl)-formamide (II) is first reacted with a mixture of phosgene and chlorine in an inert solvent at temperatures of 40°–80° C., preferably 45°–70° C., to give 2-cyanoethyl isocyanide dichloride (I) and this is then first reacted, optionally without intermediate isolation, with hydrogen chloride at −20° to 50° C., preferably 0°–30° C., and the product is then reacted with chlorine at 40°–150° C., preferably 50°–80° C.—as described above.

EXAMPLE 1

100 g (2.74 mols) of hydrogen chloride were passed into a mixture of 930 g of phosphorus oxychloride and 151 g (1.0 mol) of 2-cyanoethyl isocyanide dichloride at about 5° C. in the course of 2 hours and stirring is then continued in the same temperature range for 20 hours. After heating the suspension thus formed to 60° C, 280 g (3.94 mols) of chlorine were passed in over a period of 1.5 hours in a temperature range of 60°–70° C., whereupon the precipitate dissolved completely. A further 100 g (1.4 mols) of chlorine were then passed through the solution at 80° C. in the course of 5 hours. The entire chlorination was carried out with exclusion of light. The reaction mixture was worked up by fractional distillation under a waterpump vacuum. After stripping off the phosphorus oxychloride up to a boiling point$_{100}$ of 70° C., 196 g of distillate which, according to analysis by gas chromatography, contains 91.4% (corresponding to 179 g) of 2,4,5-trichloropyrimidine, in addition to 7.5% of phosphorus oxychloride, were obtained at a boiling point$_{12}$ of 90°–108° C.; this corresponds to a yield of 97.5% of theory.

A virtually pure product can be obtained by rectification on a column about 1 m long at a boiling point$_{12}$ of 94°–96° C.

EXAMPLE 2

150 g (4.11 mols) of hydrogen chloride were passed into a mixture of 1,150 g of 2,4,5-trichloropyrimidine and 198 g (1.31 mols) of 2-cyanoethyl isocyanide dichloride at about 25° C. in the course of 15 hours. 240 g (3.38 mols) of chlorine were then passed into the thick suspension at 60°–80° C. in the course of 3 hours, with exclusion of light, whereupon a clear, light yellow solution was formed. The internal temperature was increased up to 150° C. in the course of a further 3 hours, 20 g of chlorine per hour being passed in. Subsequent distillation under a waterpump vacuum gave, at a boiling point$_{13}$ of 95°–110° C., 1,435 g of distillate which, according to analysis by gas chromatography, consisted of 2,4,5-trichloropyrimidine to the extent of 96.3% (corresponding to 1,380 g). This corresponds to a yield of 230 g (95.5% of theory) of 2,4,5-trichloropyrimidine.

EXAMPLE 3

150 g (4.11 mols) of hydrogen chloride were passed into a mixture of 1 l of pure chloroform and 200 g (1.325 mols) of 2-cyanoethyl isocyanide dichloride at about 20° C. in the course of 15 hours. The suspension was then warmed to 60° C. and a total of 300 g of chlorine were passed in over a period of 10 hours, with exclusion of light, whereupon a clear solution was formed. The temperature was increased to 150° C. in the course of 5 hours, whilst passing in a further 20 g of chlorine/hour, chloroform simultaneously being distilled off over a column 30 cm in length. The mixture was then distilled under a waterpump vacuum. At a boiling point$_{12}$ of 90°–110° C., 178 g of distillate which, according to analysis by gas chromatography, consisted of 2,4,5-trichloropyrimidine to the extent of 6.10% (corresponding to 108.5 g) and of unreacted 2-cyanoethyl isocyanide dichloride to the extent of 38.2% (corresponding to 68 g). This corresponds to a yield of 67.6% of 2,4,5-trichloropyrimidine, relative to 2-cyanoethyl isocyanide dichloride reacted.

EXAMPLE 4

120 g (3.29 mols) of hydrogen chloride were passed into a mixture of 800 ml of thionyl chloride and 200 g (1.325 mols) of 2-cyanoethyl isocyanide dichloride at 20°–25° C. in the course of 12 hours. 240 g (3.38 mols) of chlorine were then passed into the suspension, which is readily stirrable, at 50° C. in the course of 3 hours, with exclusion of light, whereupon a clear solution was formed. The internal temperature was increased to 150° C. in the course of 5 hours whilst passing about a further 20 g of chlorine per hour, thionyl chloride simultaneously being distilled off over a column. Subsequent working up by distillation gave, at a boiling point$_{13}$ of 95°–110° C., 172 g of distillate which, according to analysis by gas chromatography, consisted of 2,4,5-tetrachloropyrimidine to the extent of 84.3% (corresponding to 145 g) and of unreacted 2-cyanoethyl isocyanide dichloride to the extent of 11.7% (corresponding to 21 g). This corresponds to a yield of 66.7% of 2,4,5-trichloropyrimidine, relative to 2-cyanoethyl isocyanide dichloride reacted.

EXAMPLE 5

Preparation of 2,4,5-trichloropyrimidine from (2-cyanoethyl)-formamide without intermediate isolation of 2-cyanoethyl isocyanide dichloride ("one-pot" process):

100 g (1.01 mols) of phosgene were dissolved in 980 g of 2,4,5-trichloropyrimidine at 45° C., and 130 g (1.325 mols) of (2-cyanoethyl)-formamide were then metered in by means of a metering pump at the same temperature in the course of 2 hours, and at the same time 158 g (2.22 mols) of chlorine and 150 g (1.51 mols) of phosgene were metered in via a flowmeter. After further stirring the mixture at 45°–50° C. for about 30 minutes, the evolution of gas had ended. The mixture was then heated to 90° C. and excess phosgene was stripped off by applying a vacuum of about 100 mm Hg.

After cooling the mixture to 25° C., 150 g (4.11 mols) of hydrogen chloride were passed in over a period of 15 hours. Chlorination was then carried out at 60°–65° C., with exclusion of light, and passing 200 g (2.82 mols) of chlorine in over a period of 2 hours changed the suspension, which was heavy to start with, into a homogeneous solution. The temperature was increased to 150° C. in the course of 4 hours whilst passing in 20 g of chlorine per hour. The mixture was then worked up by distillation. At a boiling point$_{12}$ of 92°–108° C., 1,195 g of distillate which, according to analysis by gas chromatography, consisted of 2,4,5-trichloropyrimidine to the extent of 97.9% (corresponding to 1,170 g) were obtained. This corresponds to a yield of 190 g (78.2% of theory) of 2,4,5-trichloropyrimidine.

Preparation of the starting material 2-cyanoethyl isocyanide dichloride:

(a) using thionyl chloride/chlorine 2,200 g (18.48 mols) of thionyl chloride were initially introduced into a 4 liter stirred apparatus and 453 g (4.62 mols) of (2-cyanoethyl)-formamide were added dropwise at 55° C. in the course of 4 hours, and at the same time 365 g (5.14 mols) of chlorine were passed in. After further stirring the mixture at 55°–60° C. for about 30 minutes, the evolution of gas had essentially ended. The mixture was worked up by distillation. At a boiling point$_{12}$ of 100°–110° C., 663 g of 2-cyanoethyl isocyanide dichloride were obtained in a purity, determined by gas chromatography, of 95% (corresponding to 95% of theory).

(b) using phosgene/chlorine 130 g (1.325 mols) of (2-cyanoethyl)-formamide were added dropwise to 780 g of pure chloroform, saturated at 45° C. with phosgene, at 45° C. in the course of 2 hours, and at the same time 115 g (1.67 mols) of chlorine and 105 g (1.06 mols) of phosgene were passed in. After further stirring the mixture at 50° C. for one hour, whilst passing in about a further 60 g of chlorine, the mixture was worked up by distillation. After stripping off the chloroform, 180 g of 2-cyanoethyl isocyanide dichloride were obtained at a boiling point$_{20}$ of 110°–120° C. in a purity, determined by gas chromatography, of 99.7% (corresponding to 90% of theory).

The preparation of 2-cyanoethyl isocyanide dichloride according to b) can be carried out continuously, with virtually the same yield, in a suitable reaction cascade consisting of 3 stirred flasks.

EXAMPLE 6

110 g (3.0 mols) of hydrogen chloride were dissolved in a mixture of 1,000 g of trichloropyrimidine and 151 g (1.0 mol) of 2-cyanoethyl isocyanide dichloride at 10° C. in the course of 3 hours and the mixture was then stirred for a further 12 hours. After heating the suspension thereby formed to 80° C., chlorination was carried out with about 50 g of chlorine/hour in the course of 8 hours, with exclusion of light, whereupon a clear solution was formed. 20 g of chlorine/hour were then passed into the solution at 80° C. for a further 4 hours. Working up by distillation gave, at a boiling point$_{12}$ of 94°–103° C., 1,169 g of distillate which, according to analysis by gas chromatography, consisted of 2,4,5-trichloropyrimidine to the extent of 98.2% (corresponding to 1,148 g) and of unreacted 2-cyanoethyl isocyanide dichloride to the extent of 1.5% (corresponding to 17 g). The yield of 2,4,5-trichloropyrimidine was 90.9% relative to 2-cyanoethyl isocyanide dichloride reacted.

We claim:

1. Process for the preparation of 2,4,5-trichloropyrimidine, wherein 2-cyanoethyl isocyanide dichloride is reacted with hydrogen chloride and the product is then reacted with chlorine.

2. Process according to claim 1, wherein the reaction with hydrogen chloride is carried out at −20° C. to +50° C.

3. Process according to claims 1 or 2, wherein the reaction is carried out with about 2 mols of hydrogen chloride per mol 2-cyanoethyl isocyanide.

4. Process according to claim 1, wherein the reaction with chlorine is carried out at 40°–150° C.

5. Process according to claim 1, wherein the reaction is carried out with about 2 mols of chlorine per mol 2-cyanoethyl isocyanide dichloride.

6. Process according to claim 1, wherein the reaction is carried out in the presence of an inert solvent.

7. Process according to claim 2 wherein the reaction with hydrogen chloride is carried out between 0° and 30° C.

8. Process according to claim 4 wherein the reaction with chlorine is carried out at 50°–80° C.

9. Process according to claim 6 wherein the inert solvent is 2,4,5-trichloropyrimidine or phosphorus oxychloride.

* * * * *